United States Patent
Pflaum et al.

(10) Patent No.: US 6,825,015 B1
(45) Date of Patent: Nov. 30, 2004

(54) PROCESS FOR THE OBTAINING OF HMG-COA REDUCTASE INHIBITORS OF HIGH PURITY

(75) Inventors: Zlatko Pflaum, Domzale (SI); Dusan Milivojevic, Ljubljana (SI); David Senica, Ljubljana (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 09/600,566

(22) PCT Filed: Feb. 17, 1999

(86) PCT No.: PCT/IB99/00808

§ 371 (c)(1),
(2), (4) Date: Oct. 16, 2000

(87) PCT Pub. No.: WO99/42601

PCT Pub. Date: Aug. 26, 1999

(30) Foreign Application Priority Data

Feb. 18, 1998 (SI) .......................................... P-9800046

(51) Int. Cl.⁷ ................................................. C12P 17/06
(52) U.S. Cl. .................... 435/125; 435/135; 210/656; 549/292
(58) Field of Search ................................ 435/125, 135; 210/656; 549/292

(56) References Cited

U.S. PATENT DOCUMENTS

| | | |
|---|---|---|
| 4,294,846 A | 10/1981 | Albers-Schonberg et al. .................... 424/279 |
| 4,319,039 A | 3/1982 | Albers-Schonberg ....... 560/256 |
| 4,965,200 A | 10/1990 | Chen et al. .................. 435/125 |

FOREIGN PATENT DOCUMENTS

| | | |
|---|---|---|
| EP | 0 251 625 | 1/1988 |
| WO | WO 92/16276 | 10/1992 |
| WO | WO 97/06128 | 2/1997 |
| WO | WO 97/20834 | 6/1997 |
| WO | WO 01/03647 A2 | 1/2001 |

OTHER PUBLICATIONS

Chan, C., et al. "Inhibitors of Cholesterol Biosynthesis. 1. 3,5–Dihydroxy–7–(N–imidazolyl)–6–heptenoates and heptanoates, a Novel Series of hMG–Coa Reductase Inhibitors," *J. Med. Chem.*, 1993, vol. 36, pp. 3646–3657.

Procopiou, P., et al. "Inhibitors of Cholesterol Biosynthesis. 2. 3,5–Dihydroxy–7–(N–pyrrolyl)–6–heptenoates and –heptanoates, a Novel Series of hMG–Coa Reductase Inhibitors," *J. Med. Chem,,* 1993, vol. 36, pp. 3658–3662.

*Primary Examiner*—Irene Marx
(74) *Attorney, Agent, or Firm*—Bromberg & Sunstein, LLP

(57) ABSTRACT

A process for the isolation and purification of HMG-CoA reductase inhibitors from a mycelium biomass is described, which process comprises: clarifying a mycelium broth and concentrating the clarified broth to a lower volume, acidifying of the concentrate to a pH value in the range of 4.5 to 7.5, followed by extracting the HMG-CoA reductase inhibitor with ethyl acetate, crystallization of the HMG-CoA reductase inhibitor from a water-miscible or water-soluble organic solvent, and crystallization of the HMG-CoA reductase inhibitor from an organic solvent having limited miscibility or solubility with water. The crystallization steps may also be reverse. The concept of a combination of the specified crystallization steps can also be used for the purification of a crude HMG-CoA reductase inhibitor.

23 Claims, 4 Drawing Sheets

PROCESS FOR THE OBTAINING OF HMG-COA REDUCTASE INHIBITORS OF HIGH PURITY

BACKGROUND OF THE INVENTION

Figure 1:
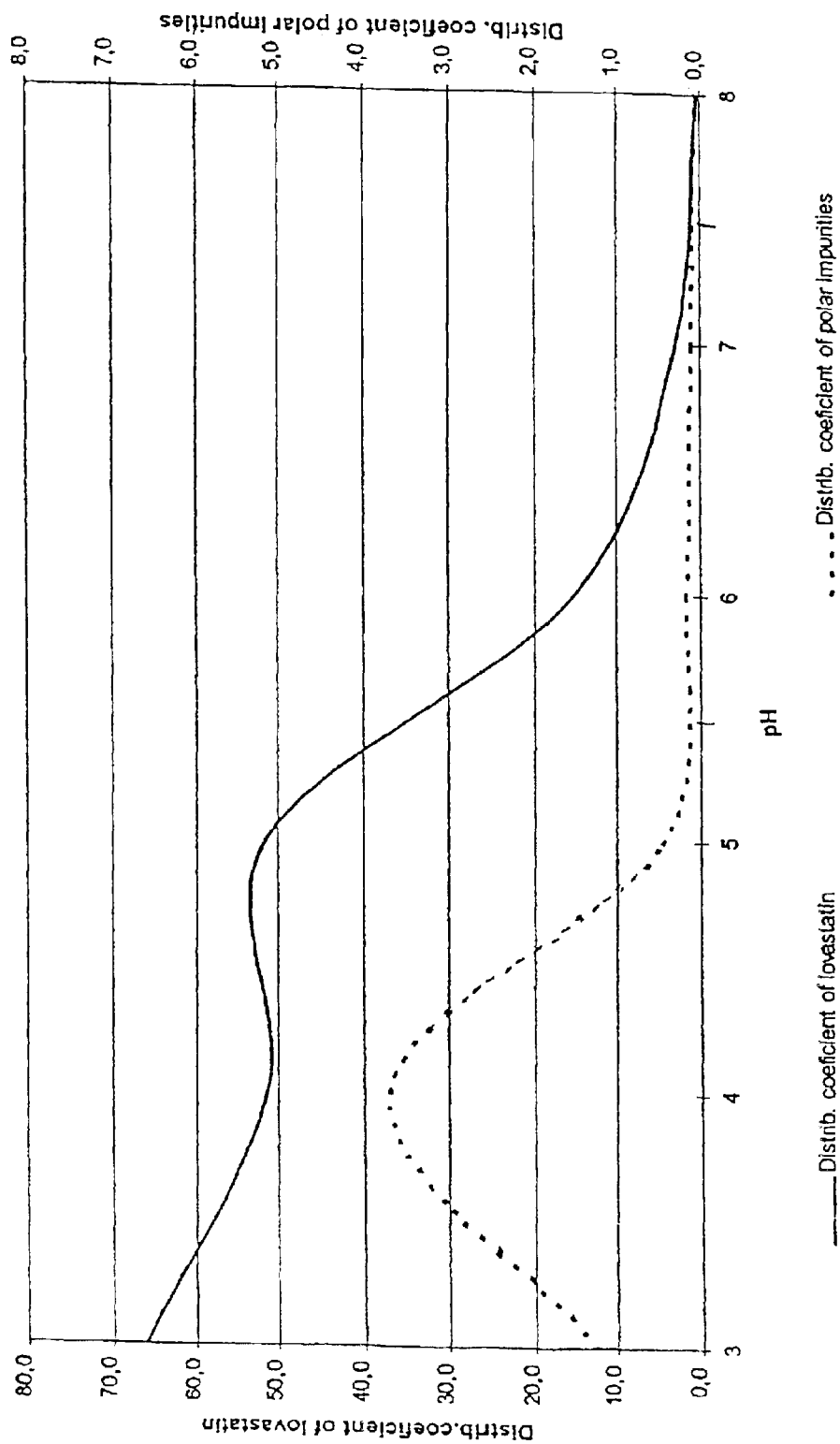

Lovastatin, pravastatin, mevastatin, simvastatin, their derivatives and analogs are known as HMG-CoA reductase inhibitors and are used as antihypercholesterolemic agents. They are produced by fermentation using microorganisms of different species identified as species belonging to Aspergillus, Monascus, Nocardia, Amycolatopsis, Mucor or Penicillium genus.

Purity of the active ingredient is an important factor for the manufacturing of a safe and effective pharmaceutical. The highest possible purity of the product is especially important if the pharmaceutical product should be taken for a longer period as is the case in the treatment or the preventing of a high plasma cholesterol. The accumulation of the impurities from the pharmaceuticals of lower purity can cause many side effects during the medical treatment.

The processes for the isolation and purification of the antihypercholesterolemic agents disclosed in the earlier patent applications comprise different combinations of extraction, chromatography, lactonization and crystallization methods. The purity of the final product obtained by these procedures is lower than 99.6%. Obtaining the product of higher purity by use of these methods is possible, but the yield of the desired product is then unacceptably low for using those methods in a large industrial scale.

The isolation process disclosed in patent application WO 92/16276 provides the solution for obtaining HMG-CoA reductase inhibitors of purity higher than 99.5%, but the use of highly sophisticated industrial high performance liquid chromatography (HPLC) equipment is required. According to the WO 92/16276 the crude HMG-CoA reductase inhibitor of approximately 85% or higher purity is dissolved in an organic solvent or in a solution of organic solvent and water. The mixture is then buffered to a pH between 2 and 9 and placed on an HPLC column. After the HMG-CoA reductase inhibitor peak of interest is collected, a portion of solvent is removed and then water is added or alternatively two-thirds of the solvent mixture are removed to crystallize the HMG-CoA reductase inhibitor. At the end the purity of the product achieved by this process is really at least 99.5% with yield of approximately 90%.

SUMMARY OF THE INVENTION

The present invention relates to a new industrial process for isolation and purification of HMG-CoA reductase inhibitors of purity higher than 99.6% and preferably higher than 99.7% from a fermentation broth. To achieve this goal an extensive study of the chemical compounds produced during the fermentation using the different species of microorganisms belonging to Aspergillus, Monascus, Nocardia, Mucor, Amnycolatopsis or Penicillium genus, their chemical properties and their behavior in the different solvents at different pH was done. Thus, the aforementioned object was solved by the process of the present invention which comprises the following steps:

clarifying a mycelium broth and concentrating the clarified broth to a lower volume, acidifying of the concentrate to a pH value in the range of 4.5 to 7.5, followed by extracting the HMG-CoA reductase inhibitor with ethyl acetate, optionally performing lactonization, performing crystallization of the HMG-CoA reductase inhibitor from a water-miscible or water-soluble organic solvent, and performing crystallization of the HMG-CoA reductase inhibitor from an organic solvent having limited miscibility or solubility with water.

DETAILED DESCRIPTION OF THE INVENTION

Figure 2:
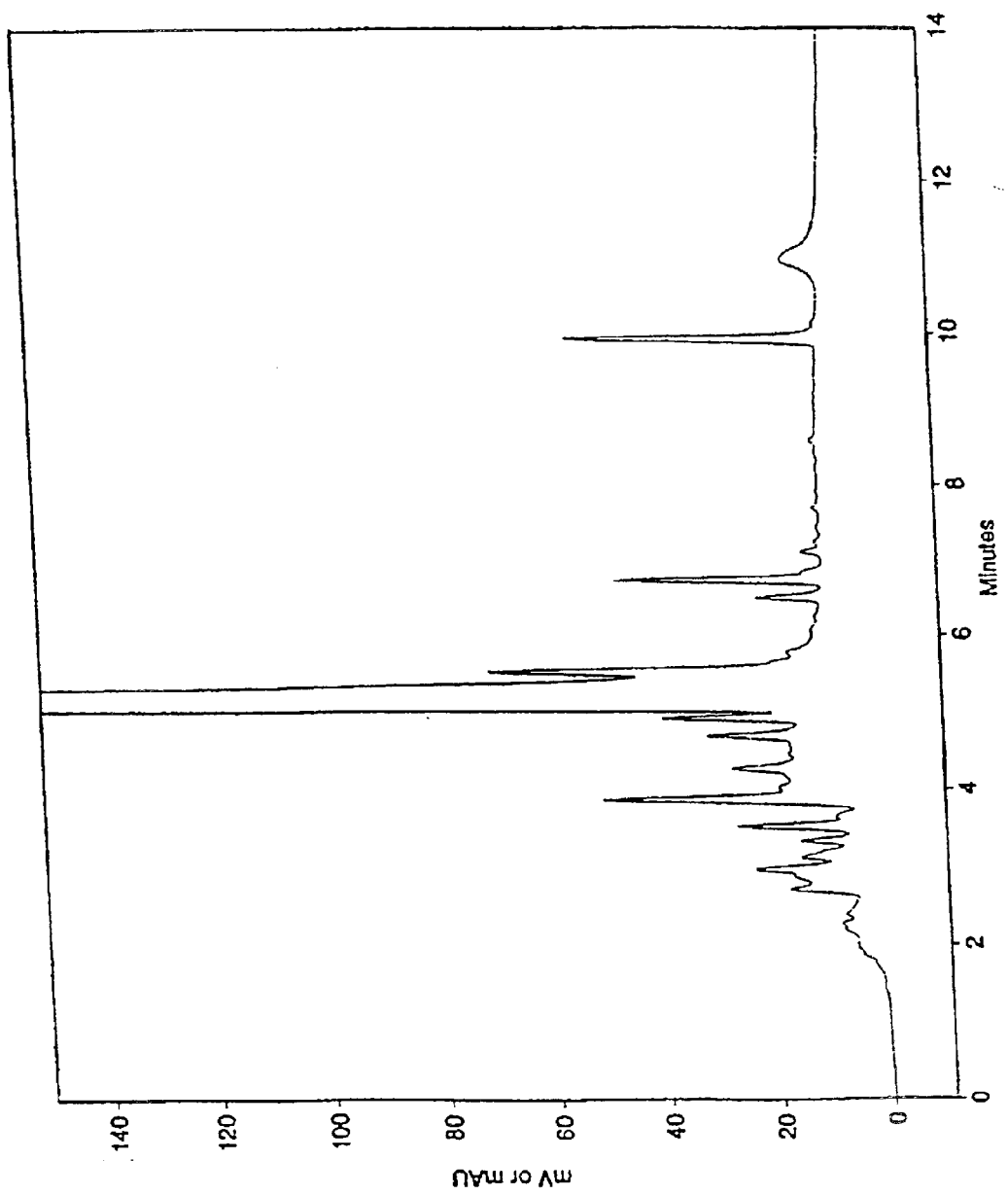
Figure 3:
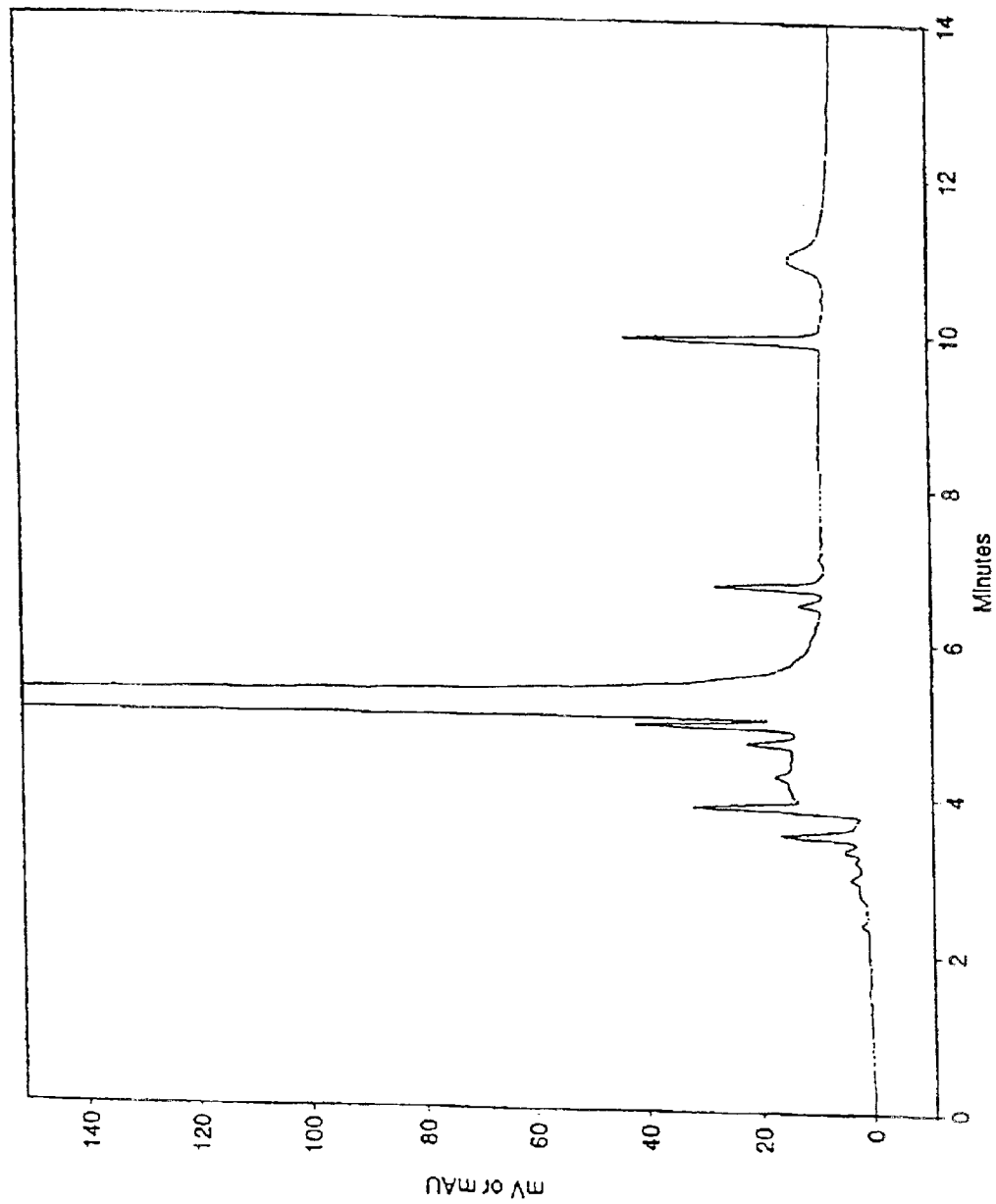
Figure 4:
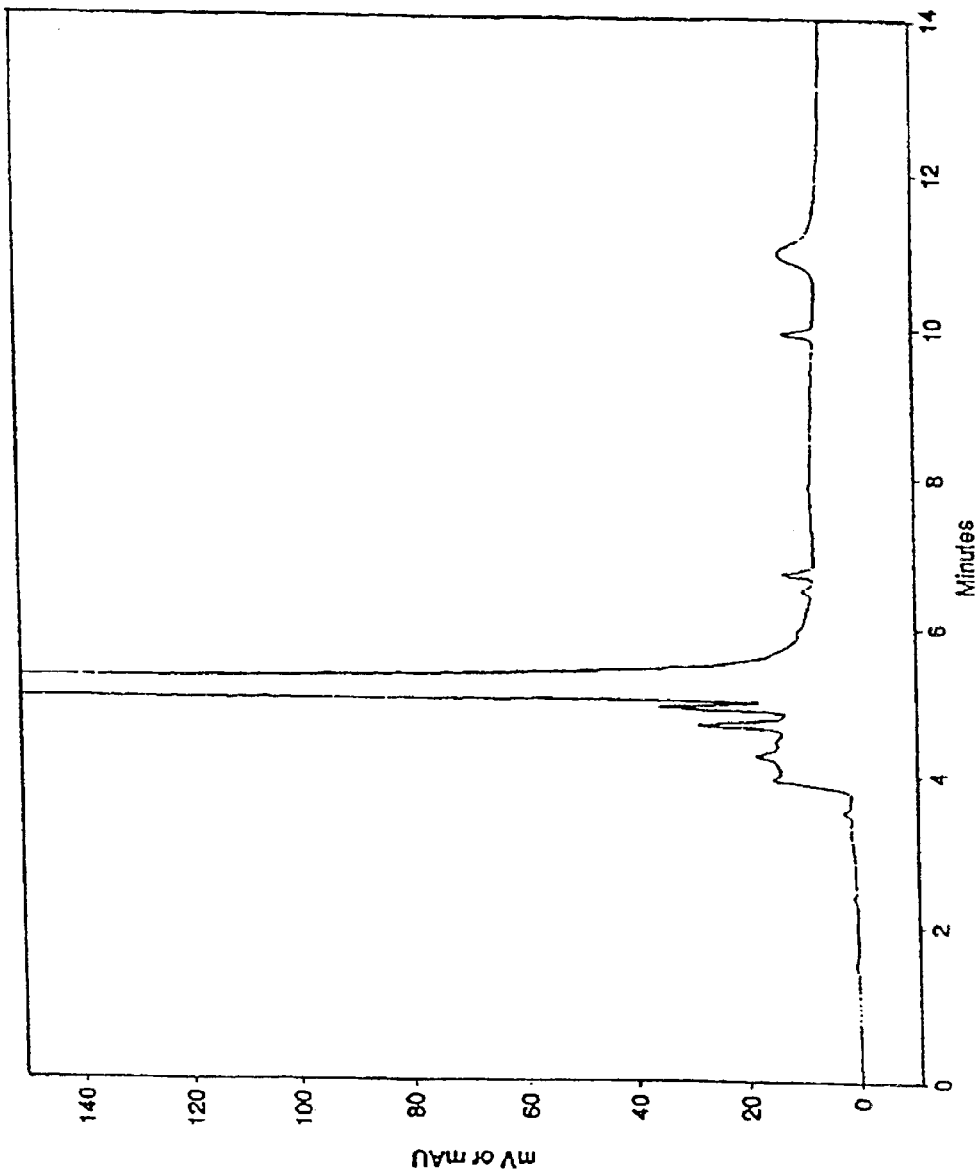

Referring to the drawings,

FIG. 1 shows the dependency from the pH of the distribution coefficient of a HMG-CoA reductase inhibitor (lovastatin) and of impurities, respectively, in the ethyl acetate extraction step, and FIGS. 2, 3 and 4 show HPLC diagrams of samples of HMG-CoA reductase inhibitor after ethyl acetate extraction as a crude composition, after crystallization from a water-miscible or water-soluble organic solvent, and after further crystallization from an organic solvent having limited miscibility or solubility with water, respectively.

Since HMG-CoA reductase inhibitors are typically both intra- and extracellular products, it is not mandatory but preferable to dissolve them effectively from the mycelium into fermentation liquor. The method for dissolution disclosed in patent application WO 97/20834 comprises treatment of fermentation broth with alkaline base to pH 11.5 and stirring for three hours. The WO 97/06128 teaches that dissolution may be done with alkalifying of the fermentation broth to pH between 10 and 13. Also a temperature between 60 and 95° C. is applied. HMG-CoA reductase inhibitors may be very efficiently dissolved from the mycelium at a pH higher than 9, but too long exposure to so rigorous condition causes the degradation of ester bond between hydroxyl group on naphthalene skeleton and carboxylic acid. Equilibrium between HMG-CoA reductase inhibitors and deacylated MMG-CoA reductase inhibitors shifts at more rigorous conditions to deacylated products. We have unexpectedly found out that the efficiency of dissolution carried out in a temperature range of 10 to 40° C., preferably in the range of 18 to 25° C., such as room temperature, for less than one hour, preferably for less than half an hour, for example for about 10 minutes, at a pH between 9.5 and 13, most preferably between 9.5 and 11.5, is equal to the efficiency achieved by less economic and more time consuming methods carried out at higher temperatures described in earlier patent applications. The dissolution may be carried out also at a pH lower than 9.5 and especially lower than 6, but the use of a huge amount of organic solvents is necessary in this case.

If this preferred embodiment of dissolving the HMG-CoA reductase inhibitor has been carried out, the fermentation broth is subsequently treated with an acidifying agent, suitably with mineral acid, to adjust the pH value between 7.5 and 8.5. Suitable mineral acids are phosphoric, sulfuric and hydrochloric acid. HMG-CoA reductase inhibitors are stable in this range of pH and the fermentation broth can be also stored for a while after this step, if that is necessary or desired.

The mycelium is removed from the fermentation broth by means of appropriate separation steps, such as filtration and/or centrifugation. Filtration is preferred, and as a filtration technique beside classic filtration also micro-, ultra- and diafiltration may suitably be used. The clarified broth is then concentrated to a lower volume, most preferably five to ten times, by means of reverse osmosis or some other methods for lowering volume.

The acidification and ethyl acetate extraction step described in the following is a significant point of the purification process.

The said concentrate is acidified by an acidifying agent, suitably with mineral acid, to a pH value between 4.5 and 7.5. Mineral acids already mentioned above as examples can be used. Then, HMG-CoA reductase inhibitor is extracted from the said pH-adjusted concentrate with ethyl acetate. Extraction is suitably done by using a counter-current extraction column. The ratio between distribution coefficients of HMG-CoA reductase inhibitors and ethyl acetate soluble impurities is the highest at a pH value from 5.5 to 7.5 and especially at a pH value from 6.0 to 7.0, and a part of polar impurities is already removed at this step. The extraction carried out at pH value lower than 5.0, especially lower than 4, is more efficient, because of higher distribution coefficient of HMG-CoA reductase inhibitors, but it results in high level of polar impurities. The distribution coefficients of ethyl acetate soluble impurities are also high at that pH value, as is shown in FIG. 1. The extraction into ethyl acetate carried out at a pH value between 4.5 and 7.5, especially above 5.0 and in particular above 5.5, results in lower level of polar impurities because of their low distribution coefficients. Worse distribution of HMG-CoA reductase inhibitors from the concentrate into ethyl acetate at that pH value can be compensated with a longer counter-current extraction column.

If desired, the resulted ethyl acetate extract is then concentrated and HMG-CoA reductase inhibitor is lactonized optionally at this stage of the process. At pH between 5.5 and 7.5, the major part of the HMG-CoA reductase inhibitor is in free acid form. Therefore, the concentration and lactonization may be omitted if HMG-CoA reductase inhibitor is not used in the pharmaceutical as a lactone. The lactonization is suitably done by contacting the HMG-CoA reductase inhibitor with catalytic amount of mineral or organic acid, most preferably trifluoracetic acid (TFA). The HMG-CoA reductase inhibitor which is optionally lactonized may then be directly crystallized from ethyl acetate, as will be described below. Alternatively, the ethyl acetate is removed, suitably by vaporization, and a crude HMG-CoA reductase inhibitor product, which is optionally lactonized, is obtained.

The thus obtained crude HMG-CoA reductase inhibitor may then optionally be subjected to adsorption chromatography, preferably to reversed phase chromatography. As the mobile phase for adsorption chromatography, acetonitrile or lower alcohols such as methanol, ethanol or propanol, or a mixture of these solvents with water, can suitably be used. Preferably, the crude HMG-CoA reductase inhibitor is dissolved in pure acetonitrile or mixture acetonitrile/water with at least 30% volume/volume (v/v) of acetonitrile, and the resulting solution is placed on an adsorption chromatography column. The column packing include, but are not limited to stationary phases based on octylsilane, dimethylsilane, octadecylsilane, cyano-silane, polystyrenedivinylbenzene copolymer or acrylic polymer. Other typical stationary phase materials may also be used, for example silica, alumina, or the like. The adsorbed compounds are eluted with an appropriate mobile phase, such as acetonitrile/water gradient. The HMG-CoA reductase inhibitor peak of interest is collected and the mobile phase solvent is removed to crystallize the HMG-CoA reductase inhibitor. The purity of crystallized crude HMG-CoA reductase inhibitors is between 80% and 92% and depends on impurity profile in the fermentation broth. The optional adsorption chromatography may also be replaced by normal chromatography, flash chromatography, industrial HPLC, or by methods of extraction or crystallization.

The combined crystallization treatment which is peculiar according to the present invention will be described in more detail in the following. More specifically, it comprises crystallization of the HMG-CoA reductase inhibitor from an organic solvent being water-miscible or water-soluble, and crystallization of the HMG-CoA reductase inhibitor from an organic solvent having a limited miscibility or solubility with water. The order of both crystallizations may also be inverse. The property of the organic solvent of being either water-miscible or water-soluble, or having a limited miscibility or solubility with water is per se known to the one skilled in the art and is, for example, described in "Ullmann's Encyclopedia of Industrial Chemistry", Vol. A24, 5$^{th}$ edition (1993), pp. 437–505, incorporated herein by reference. In the meaning of the present invention, the term "water-miscible or water-soluble" shall refer to organic solvents which show essentially unlimited, preferably 100% miscibility or solubility with water, and the term "limited miscibility or solubility with water" shall also include water-immiscible or water-insoluble organic solvents. Furthermore, the concept of crystallization of the present invention in particular also includes precipitation.

Examples for essentially water-miscible or water-soluble organic solvents include: low alkyl alcohols such as methanol, ethanol, propanol and isopropyl alcohol, low alkyl ketones such as acetone and methyl ethyl ketone, low alkyl glycol ethers such as methyl glycol, ethyl glycol, propyl glycol and ethyl diglycol, and dipolar aprotic solvents such as N,N-dimethyl-formamide (DMF), N,N-dimethylacetamide (DMA) and dimethyl sulfoxide (DMSO), including mixtures of these solvents. As particularly preferred examples for the water-miscible organic solvent, acetone and low alkyl alcohols are mentioned. Examples for an organic solvent having limited miscibility or solubility with water include: higher alkyl alcohols such as butanol, isobutanol amyl alcohol, hexanol, 2-ethylhexanol, benzyl alcohol and cyclohexanol, higher alkyl ketones such as methylbutyl ketone, methyl isobutyl ketone and cyclohexanone, esters such as methyl acetate, ethyl acetate, n-propyl (and isopropyl) acetate, n-butyl (and iso-butyl or sec-butyl) acetate and amyl acetate, ethers such as diethyl ether and diisopropyl ether, chlorinated hydrocarbons such as methylene chloride and chloroform, and the like, including mixtures of these solvents. Particularly preferred as a solvent having limited miscibility or solubility with water is ethyl acetate.

We have unexpectedly found out that the crystallization of HMG-CoA reductase inhibitors from water-miscible organic solvent like acetone or low alkyl alcohol followed by further recrystallizations with the same solvent can remove only a minor part of nonpolar and a major part of polar impurities, and the crystallization from organic solvent having a limited miscibility with water like ethyl acetate followed by further recrystallizations from the same solvent removed only major nonpolar impurities. The last fact is clearly evident from HPLC diagrams of crude HMG-CoA reductase inhibitor (FIG. 2), HMG-CoA reductase inhibitor after the crystallization from acetone (FIG. 3) and HMG-CoA reductase inhibitor obtained by the crystallization from acetone and further recrystallized from ethyl acetate (FIG. 4). According to this unexpected recognition, the last step of the present invention comprising combined crystallization from water-miscible or water-soluble organic solvent and from an organic solvent having limited miscibility or solubility with water cannot be omitted in the process for achieving HMG-CoA reductase inhibitors of high purity.

The combined crystallization treatment according to the present invention may be effected as follows. First, the crystals of crude HMG-CoA reductase inhibitor are dissolved in the afore-mentioned substantially (preferably 100%) water-miscible or water-soluble organic solvent, in particular acetone or lower alcohol, and then water is added to let HMG-CoA reductase inhibitor crystallize or precipitate. Alternatively, the crude HMG-CoA reductase inhibitor being dissolved in the substantially water-miscible or water-soluble organic solvent is added to water for being crystallized or precipitated. These procedures may be repeated again with the same or another water-miscible or water-soluble organic solvent, if necessary, for example from one to four times depending on the purity of the starting crude material.

The crystals obtained thereby are then dissolved in the afore-mentioned solvent having limited miscibility or solubility with water, like ethyl acetate, to an appropriate concentration which preferably lies in the range of 10 to 35 g/l, most preferably in the range of 15 to 25 g/l. After the removal of one-third to three-fourth of solvent, the HMG-CoA reductase inhibitor crystallizes. Crystallization from the same or another organic solvent having limited miscibility or solubility with water may be repeated, if necessary, for example for one to three times depending on the purity of the product obtained by crystallization from water-miscible or water-soluble organic solvent. The crystallized HMG-CoA reductase inhibitor is then filtered and dried to yield a product of purity of at least 99.6%.

As already mentioned, the order of crystallizations may be inverse, i.e. first performing crystallization from the organic solvent having limited miscibility or solubility with water, and then performing crystallization from the water-miscible or water-soluble organic solvent. In a preferred embodiment of the present invention, first performing crystallization from ethyl acetate as the organic solvent having limited miscibility or solubility with water may suitably be effected directly after the ethyl acetate extraction step or, optionally, after the lactonization step described above.

With the process according to the present invention, products having a purity of at least 99.6% and even at least 99.7% are achievable.

In a further alternative embodiment, the different kinds of crystallizations may be performed repeatedly in an alternating manner.

In another aspect of the present invention, the previously described process of combined crystallization steps from water-miscible or water-soluble organic solvent and from organic solvent having limited miscibility or solubility with water are employed as a final polishing step of any process for isolation and/or purification of HMG-CoA reductase inhibitors. Accordingly, such a final polishing step can also be applied to raw materials of HMG-CoA reductase inhibitor which have been conventionally obtained. The thus achievable purity of HMG-CoA reductase inhibitor is at least 99.6% and even at least 99.7%.

The process according to the present invention is well suited especially when lovastatin is selected as the HMG-CoA reductase inhibitor. Accordingly in another aspect of the present invention, the process described above is used for the isolation and/or purification of lovastatin.

The essentially pure HMG-CoA reductase inhibitors obtained by the process according to the present invention, such as lovastatin, mevastatin, pravastatin and simvastatin as well as their derivatives and analogues, can be beneficially used for the preparation of a pharmaceutical for the prevention and/or treatment of diseases. The obtained inhibitors and pharmaceuticals are particularly useful as medicaments or preventives for reducing the risk of stroke, transient ischemic attack, atherosclerosis and myocardial infarction.

The following examples illustrate the process of the instant invention and are not to be considered as limiting the invention set forth in the claims appended hereto.

EXAMPLES

Example 1

Fermentation broth (160 l) with concentration of lovastatin 1 g/l obtained by fermentation with *Aspergillus terreus* ATCC 20542 was placed into the vessel (400 l) and adjusted to pH 10 with 1 M aqueous sodium hydroxide solution. After 10 minutes of intensive stirring at room temperature the broth was adjusted to pH 9 with 1 M sulfuric acid solution and the biomass was filtered off. The filtrate was then acidified with 1 M sulfuric acid solution to pH 6.5. 160 l of ethyl acetate was added to filtrate and the obtained mixture was stirred for 20 min. The aqueous and ethyl acetate phases were separated by extraction centrifuge. The ethyl acetate extract was concentrated in rotary evaporator to volume of 14 l. The concentration of the lovastatin in the free acid form in the ethyl acetate concentrate amounted to 10 g/l.

The ethyl acetate concentrate (14 l) was then placed into reactor (40 l) and lactonized. The lactonization was initiated by catalytic amount of TFA (0.5 ml of TFA/1 l of concentrate). The lactonization procedure lasted for two hours at 40° C. The concentrate was washed after the lactonization two times with 14 l of 5% ammonium hydrogen carbonate aqueous solution. The aqueous phase was discharged, the organic phase was further concentrated to dry in rotary evaporator. The resulted oily product (1.5 l) contained 133 g of lovastatin.

The obtained oily product (161 ml) was dissolved in 80 ml of acetonitrile and loaded on a chromatography column (80 cm, 3.6 cm) filled with XAD-16 (XAD-16 is the commercial name of company Rohm & Hass, 20–50 mesh). The column was eluted first with 40:60 acetonitrile/water (pH 3, adjusted by hydrochloric acid) at a rate of 75 ml/min. Elution was monitored by UV detector (236 nm) and after first drop of absorption the elution of the column with 55:45 acetonitrile/water (pH 3, adjusted by hydrochloric acid) was started. The main fraction was collected and after the fall of the absorption the column was washed with 80:20 acetonitrile/water (pH 3, adjusted by hydrochloric). The acetonitrile was removed from the main fraction by rotary evaporator (50° C., 150 mbar) and the resulted crystals were filtered off. Mass of crystals was 24.5 g and the content of lovastatin was 50% weight/weight (w/w). HPLC purity was 92.5%.

Resulted crystals (24 g) were dissolved in 350 ml acetone and 700 ml water was added under continuous stirring. The mixture was placed on 4° C. for 30 minutes. Obtained crystals were filtered off and dried in vacuo at room temperature. Mass of crystals was 12.7 g with the content 90% w/w of lovastatin. HPLC purity was 98.8%. The crystallization from acetone was repeated under the same condition and 11.3 g of crystals with 97% w/w of lovastatin were obtained. HPLC purity was 99.4%.

The crystals (11.3 g) obtained after the second crystallization from acetone were dissolved in 700 ml of ethyl acetate and the ethyl acetate was evaporated in vacuo to the concentration of lovastatin 70 g/l. The concentrate was placed on 8° C. for one hour. Resulted crystals of lovastatin were filtered off and then dried in vacuo. Mass of crystals was 9.4 g with 99.6% w/w content of lovastatin. HPLC purity was 99.7%.

Example 2

Lovastatin crystals (3 g), isolated after the XAD-adsorption chromatography as described in Example 1, were dissolved in 170 ml ethyl acetate. The ethyl acetate was evaporated in vacuo (200 mbar) at 50° C. to 35 ml. The concentrate was placed on 10° C. for one hour. Resulted crystals of lovastatin were filtered off and then dried in vacuo. Mass of crystals was 2.1 g with 96% w/w content of lovastatin. HPLC purity was 99.0%.

The obtained crystals (2.1 g) were dissolved in 50 ml acetone and 85 ml water was added. The mixture was placed then on 10° C. for 30 minutes and the crystals were filtered off and dried in vacuo at 40° C. Mass of resulted crystals was 1.9 g with the 99% w/w of lovastatin. HPLC purity was 99.8%.

Example 3

A fermentation broth (30 l in a 50 l fermentor) containing pravastatin (690 g per kg of fermentation broth; HPLC purity of pravastatin was 48.7%) was filtered and the resulting mycelium was washed with water. Filtrate (51 l) was acidified to pH 5.0 with 10% aqueous solution of phosphoric acid. Active substance (pravastatin) was then extracted in an extraction column from the filtrate into 70 l of ethyl acetate. Water phase (50 l) with less than 2 g of pravastatin and with major part of impurities was discharged. The ethyl acetate phase was evaporated to 800 ml and used further in the process of isolation. The HPLC purity of pravastatin in the ethyl acetate extract was 70.3%. For further isolation, the oily product was subjected to adsorption chromatography and combined crystallization steps in accordance with Example 1.

Example 4

A crude simvastatin (2.3 g) in lactone form was dissolved in acetone (7 ml) and 15 ml of water was added. The result was oily product that crystallized next in 10 minutes. The obtained crystals were then filtered, washed with water and dried at 40° C. for 60 min. The resulted crystals (2.2 g) with HPLC purity of 99.51% were then dissolved in ethyl acetate (8 ml). The resulted solution was concentrated to 4 ml, and simvastatin was left to crystallize for 60 min at 8° C. The product was filtered and washed with water. The crystals were then dried at 40° C. for 60 min. The purity of the resulted simvastatin (1.7 g) was 99.73%.

Example 5

A crude mevastatin (2.0 g) in lactone form with HPLC purity 98.5% was dissolved in acetone (7 ml) and 20 ml of water was added. The result was oily product that crystallized next in 10 min. The obtained crystals were then filtered, washed with water and dried at 40° C. for 60 min. The resulted crystals (1.8 g) with HPLC purity 99.33% were then dissolved in ethyl acetate (8 ml). The resulted solution was concentrated to 4 ml and mevastatin was left to crystallize for 60 min at 8° C. The product was filtered and washed with water. The crystals were then dried at 40° C. for 60 min. The purity of the resulted mevastatin (1.3 g) was 99.72%.

What is claimed is:

1. A process for the isolation and purification of HMG-CoA reductase inhibitors from mycelium biomass which comprises:

clarifying a mycelium broth and concentrating the clarified broth to a lower volume,
acidifying the concentrate to a pH value in the range of 4.5 to 7.5, followed by extracting the HMG-CoA reductase inhibitor with ethyl acetate;
optionally performing lactonization;
crystallizing the HMG-CoA reductase inhibitor from:
  i) a water-miscible first organic solvent; and
  ii) ii) a second organic solvent having limited miscibility or solubility with water selected from the group consisting of n-butanol, isobutanol, amyl alcohol, hexanol, 2-ethylhexanol, benzyl alcohol, cyclohexanol, methylbutyl ketone, methyl isobutyl ketone, cyclohexanone, methyl acetate, ethyl acetate, n-propyl acetate, isopropyl acetate, isobutyl acetate, sec-butyl acetate, amyl acetate, diethyl ether, diisopropyl ether, methylene chloride, chloroform, and mixtures of these solvents.

2. The process according to claim 1, further comprising, before clarifying the mycelium biomass broth:
dissolving the HMG-CoA reductase inhibitor from a mycelium biomass at a pH value between 9.5 and 13 into fermentation liquor, and
adjusting the broth to a pH value between 7.5 and 8.5.

3. The process according to claim 2, wherein the dissolving step is carried out at a temperature in the range of 10 to 40° C. for less than one hour.

4. The process according to claim 1, wherein clarifying the mycelium broth is carried out by removing the mycelium from the broth by means of filtration.

5. The process according to claim 1, wherein said clarified broth is concentrated by means of reverse osmosis.

6. The process according to claim 1, wherein the concentrate is acidified to pH value in the range 5.6 to 7.5.

7. The process according to claim 1, wherein the concentrate is acidified to a pH value in the range 6.0 to 7.0.

8. The process according to claim 1, wherein the HMG-CoA reductase inhibitor which is extracted from ethyl acetate and optionally lactonized is subjected to a purification step by absorption chromatography.

9. The process according to claim 8, wherein a mixture of acetonitrile and water is used as the mobile phase for adsorption chromatograpy.

10. The process according to claim 1, wherein the order of the crystalization steps is reversed.

11. The process according to claim 1, wherein the water-miscible first organic solvent used in the crystallization step is acetone or a low alkyl alcohol.

12. The process according to claim 1, wherein the crystallization step from a water-miscible first organic solvent comprises dissolving the HMG-CoA reductase inhibitor in acetone, and then adding water thereto.

13. The process according to claim 1, wherein the crystallization step from a second organic solvent comprises dissolving the HMG-CoA reductase inhibitor in said organic solvent at a concentration of 10 to 35 g/L, and removing one-third to three-fourths of said organic solvent.

14. The process according to claim 1, wherein the second organic solvent used in the crystallization step is ethyl acetate.

15. The process according to claim 1, wherein HMG-CoA reductase inhibitors are obtained having a purity higher than 99.6%.

16. The process according to claim 15, wherein the HMG-CoA reductase inhibitors having a purity higher than 99.6% are selected from the group consisting of lovastatin, pravastatin, simvastatin and mevastatin.

17. The process according to claim 1, wherein the HMG-CoA reductase inhibitor is selected from the group consisting of lovastatin, pravastatin and mevastatin.

18. A process for the purification of HMG-CoA reductase inhibitors which comprises subjecting the HMG-CoA reductase inhibitor to combined crystallization steps, which consist of crystallization from a water-miscible first organic solvent and crystallization from a second organic solvent which is selected from the group consisting of n-butanol, isobutanol, amyl alcohol, hexanol, 2-ethylhexanol, benzyl alcohol, cyclohexanol, methylbutyl ketone, methyl isobutyl ketone, cyclohexanone, methyl acetate, ethyl acetate, n-propyl acetate, isopropyl acetate, isobutyl acetate, sec-butyl acetate, amyl acetate, diethyl ether, diisopropyl ether, methylene chloride, chloroform, and mixtures of these solvents.

19. The process according to claim 18, wherein the obtained HMG-CoA reductase inhibitors have purity higher than 99.7%.

20. The process according to claim 18, wherein acetone or a low alkyl alcohol is used as the water-miscible organic solvent.

21. The process according to claim 18, wherein the crystallization from a water-miscible organic solvent comprises dissolving the HMG-CoA reductase inhibitor in acetone, and then adding water thereto.

22. The process according to claim 18, wherein said crystallization from a second organic solvent comprises dissolving the HMG-CoA reductase inhibitor in said second organic solvent at a concentration of 10 to 35 g/L, and removing one-third to three-fourths of said organic solvent.

23. The process according to claim 18, wherein ethyl acetate is used as the second organic solvent.

\* \* \* \* \*